(12) United States Patent
Commereuc et al.

(10) Patent No.: US 6,828,269 B2
(45) Date of Patent: Dec. 7, 2004

(54) CATALYTIC COMPOSITION AND A PROCESS FOR OLIGOMERIZING ETHYLENE, IN PARTICULAR TO 1-HEXENE

(75) Inventors: Dominique Commereuc, Meudon (FR); Sébastien Drochon, Rueil Malmaison (FR); Lucien Saussine, Croissy sur Seine (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 702 days.

(21) Appl. No.: 09/745,441

(22) Filed: Dec. 26, 2000

(65) Prior Publication Data

US 2001/0023281 A1 Sep. 20, 2001

(30) Foreign Application Priority Data

Dec. 24, 1999 (FR) .............................. 99 16509

(51) Int. Cl.[7] .............................. C08F 2/00; C08F 4/00; C08F 4/50; B01J 31/34; B01J 37/00
(52) U.S. Cl. .................. 502/117; 502/113; 502/132; 502/150; 502/169; 502/171; 502/226; 502/306; 502/340; 526/89; 526/123.1; 526/124.3
(58) Field of Search .................. 502/117, 154, 502/113, 114, 115, 118, 121, 125, 128, 132, 133, 150, 169, 171, 172, 226, 228, 306, 305, 340, 341; 526/89, 90, 123.1, 124.3

(56) References Cited

U.S. PATENT DOCUMENTS

| 4,024,050 A | * | 5/1977 | Shell et al. ............. 208/48 AA |
| 4,250,284 A | * | 2/1981 | Delbouille et al. ....... 526/124.2 |
| 4,422,957 A | * | 12/1983 | Kaus et al. ................. 502/105 |
| 4,547,475 A | * | 10/1985 | Glass et al. ................. 502/115 |

FOREIGN PATENT DOCUMENTS

| EP | 0 808 849 | 11/1997 |
| GB | 1 309 987 | 3/1973 |
| GB | 1554340 | * 10/1979 |

* cited by examiner

Primary Examiner—Michael La Villa
(74) Attorney, Agent, or Firm—Millen, White, Zelano & Branigan, P.C.

(57) ABSTRACT

A catalytic composition is obtained by mixing at least one chromium compound with at least one aryloxy compound of an element M selected from the group formed by magnesium, calcium, strontium and barium, with general formula $M(RO)_{2-n}X_n$, where RO is an aryloxy radical containing 6 to 80 carbon atoms, X is a halogen or a hydrocarbyl radical containing 1 to 30 carbon atoms and n is a whole number that can take values of 0 to 2, and with at least one aluminum compound selected from hydrocarbylaluminum compounds (tris(hydrocarbyl)-aluminum, chlorinated or brominated hydrocarbylaluminum compounds) and aluminoxanes. The catalytic composition can be used in an ethylene oligomerization process, in particular to produce 1-hexene.

33 Claims, No Drawings

CATALYTIC COMPOSITION AND A PROCESS FOR OLIGOMERIZING ETHYLENE, IN PARTICULAR TO 1-HEXENE

The present invention relates to a process for oligomerizing ethylene, in particular to 1-hexene, and to the catalytic composition used.

Processes for producing alpha olefins from ethylene generally result in a series of oligomers containing 4 to 30 carbon atoms and even more than 30 carbon atoms, and the olefins are then separated by distillation. The demand for lower olefins, essentially 1-butene, 1-hexene and 1-octene, has been increasing over the past few years; they are used in particular as co-monomers with ethylene in the production of linear low density polyethylene.

Only a few catalysts exist that can selectively lead to the formation of a particular oligomer, as is the case when dimerizing ethylene to butene-1 with a titanium-based catalyst. However, chromium-based catalysts are known to result in the principal formation of 1-hexene, with more or less polyethylene, the proportion of butenes and octenes in the products being very low. (R. M. Manyik, W. E. Walker, T. P. Wilson, J. Catal., 1977, 47, 197 and J. R. Briggs, J. Chem. Soc., Chem. Commun. 1989, 674 and cited references). Catalysts for more or less selective ethylene trimerization have been claimed, for example, in U.S. Pat. Nos. 5,198,563, 5,288,823, and 5,382,738, European patent applications Nos. 0 608 447, 0 611 743 and 0 614 865. Such catalysts are prepared from a chromium salt and a metallic amide, in particular a pyrrole. Other catalysts use an aluminoxane and a chromium complex with a chelating phosphine (U.S. Pat. No. 5,550,305).

French patent application 2 764 524 describes a catalytic composition obtained by mixing at least one chromium compound with at least one aluminum aryloxy compound and at least one hydrocarbylaluminum compound, that has a particular selectivity for the formation of butene-1 and/or 1-hexene by ethylene oligomerization.

It has now been discovered that a catalytic composition obtained by mixing at least one chromium compound with at least one aryloxy compound of an element M selected from the group formed by magnesium, calcium, strontium and barium and with at least one hydrocarbylaluminum compound, has a particular selectivity for the formation of 1-hexene by ethylene oligomerization.

More precisely, said catalytic composition is obtained by mixing:

at least one chromium compound that can comprise one or more identical or different anions selected from the group formed by halides, carboxylates, acetylacetonates, alkoxy and aryloxy anions;

with at least one aryloxy compound of an element M selected from the group formed by magnesium, calcium, strontium and barium, with general formula $M(RO)_{2-n}X_n$, where RO is an aryloxy radical containing 6 to 80 carbon atoms, X is a halogen or a hydrocarbyl radical containing 1 to 30 carbon atoms and n is a whole number that can take values of 0 to 2;

and with at least one aluminum compound selected from hydrocarbylaluminum compounds with general formula $AlR'_mY_{3-m}$, where R' is a hydrocarbyl radical containing 1 to 6 carbon atoms, Y is a chlorine or bromine atom and m is a number from 1 to 3 (i.e., tris(hydrocarbyl)-aluminum compounds, chlorinated or brominated hydrocarbylaluminum compounds) and aluminoxanes.

The chromium compound can be a chromium (II) or chromium (III) salt, but also a salt with a different oxidation number that can comprise one or more identical or different anions such as halides, carboxylates, acetylacetonates or alkoxy or aryloxy anions. The chromium compounds preferably used in the invention are chromium (III) complexes as they are more accessible, but a chromium (I) compound or chromium (II) compound may also be suitable.

The chromium compounds selected can advantageously be dissolved in a hydrocarbon medium by complexing with an organic oxygen-containing compound such as an ether, an ester or a compound selected from acetates and ketals (these latter resulting from condensation of an aldehyde or a ketone with a monoalcohol or a polyalcohol) such as 2,2-di(2-ethylhexyloxy)propane.

The aryloxy compound of element M is selected from the group formed by magnesium, calcium, strontium and barium, with (general formula $M(RO)_{2-n}X_n$, where RO is an aryloxy radical containing 6 to 80 carbon atoms. X is a halogen (chlorine or bromine) or a linear or branched hydrocarbyl radical containing 1 to 30 carbon atoms, for example alkyl, cycloalkyl, alkenyl, aryl, aralkyl, substituted aryl or substituted cycloalkyl, preferably a hydrocarbyl residue containing 2 to 10 carbon atoms, and n is a whole number that can take values of 0 to 2.

Preferred aryloxy compounds of element M comprise an aryloxy radical RO with general formula:

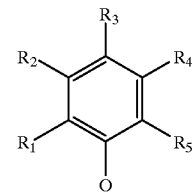

where $R_1$, $R_2$, $R_3$, $R_4$ and $R_5$, which may be identical or different, each represent a hydrogen atom, a halogen atom or a hydrocarbyl radical, for example alkyl, cycloalkyl, alkenyl, aryl, or aralkyl, substituted aryl or cycloalkyl, preferably containing 1 to 16 carbon atoms, more particularly 1 to 10 carbon atoms. Non limiting examples of $R_1$, $R_2$, $R_3$, $R_4$ and $R_5$ are methyl, ethyl, n-propyl, ispropyl, n-butyl, tert-butyl, cyclohexyl, benzyl, phenyl, 2-methylphenyl, 2,6-dimethylphenyl, 2,4,6-trimethlylphenyl, or 2-methyl-2-phenylprop-1-yl residues.

Non-limiting examples of preferred aryloxy radicals that can be cited are: 4-phenylphenoxy, 2-phenylphenoxy, 2,6-diphenylphenoxy, 2,4,6-triphenylphenoxy, 2,3,5,6-tetraphenylphenoxy, 2-tert-butyl-6-phenylphenoxy, 2,4-di-tert-butyl-6-phenylphenoxy, 2,6-diisopropyphenoxy, 2,6-dimethylphenoxy 2,6-di-tert-butylphenoxy, 4-methyl-2,6-di-tert-butylphenoxy, 2,6-dichloro-4-tert-butylphenoxy and 2,6-dibromo-4-tert-butylphenoxy. When the aryloxy compound of element M is selected from aryloxides with general formula $M(RO)_2$, the two aryloxy radicals can be carried by the same molecule, for example the biphenoxy radical, the binaphthoxy radical or the 1,8-naphthalene-dioxy radical, which may or may not be substituted by one or more alkyl, aryl or halogen radicals.

The preparation of the compound $M(RO)_{2-n}X_n$ is known in the literature. Any process for preparing this compound is suitable, such as reacting a phenol ROH with a dialkylmetallic element in an organic solvent, for example a hydrocarbon or an ether.

The aluminum compounds used in the invention are selected from hydrocarbylaluminum-tris(hydrocarbyl)

aluminum compounds, chlorinated or brominated hydrocarbylaluminum compounds and aluminoxanes. The tris(hydrocarbyl)aluminum compounds and chlorinated or brominated compounds of hydrocarbylaluminum are represented by general formula $AlR'_mY_{3-m}$ where R' is a hydrocarbyl radical, preferably alkyl, containing 1 to 6 carbon atoms, Y is a chlorine or bromine atom, preferably a chlorine atom, and m is a number from 1 to 3. Non-limiting examples that can be cited are: dichloroethylaluminum, ethylaluminum sesquichloride, chlorodiethyl-aluminum, chlorodiisobutylaluminum, triethylaluminum, tripropylaluminum, triisobutylaluminum and methylaluminoxane. The preferred hydrocarbylaluminum compound is triethylaluminum.

The catalyst components can be brought into contact in a solvent comprising at least one saturated hydrocarbon such as hexane, cyclohexane, heptane, butane or isobutane, at least one unsaturated hydrocarbon such as a mono-olefin or a diolefin containing 4 to 20 carbon atoms, for example, and/or at least one aromatic hydrocarbon such as benzene, toluene, ortho-xylene, mesitylene or ethylbenzene.

The chromium concentration in the catalytic solution can be in the range $1 \times 10^{-5}$ to 0.1 mole/l, preferably $5 \times 10^{-5}$ to $1 \times 10^{-2}$ mole/l. The mole ratio between the aryloxy compound of element M and the chromium compound can be from 1:1 to 30:1, preferably 1:1 to 20:1. The mole ratio between the hydrocarbylaluminum and the chromium compound is in the range 1:1 to 35:1, preferably 1:1 to 15:1.

The order of mixing the three constituents of the catalytic composition is not critical. However, the chromium compound is preferably mixed first with the aryloxy compound of element M, and then the hydrocarbylaluminum compound is added.

The ethylene oligomerization reaction can be carried out at a total pressure of 0.5 to 15 MPa, preferably 1 to 8 MPa, and at a temperature of 20° C. to 180° C., preferably 50° C. to 160° C.

In a particular batchwise implementation of the catalytic oligomerization reaction, prepared as described above, a set volume of the catalytic solution, prepared as described above, is introduced into a reactor provided with the usual stirring, heating and cooling means, then pressurized to the desired pressure with ethylene, and the temperature is adjusted to the desired value. The oligomerization reactor is then kept at a constant pressure by introducing ethylene until the total volume of the liquid produced represents, for example, 2 to 50 times the volume of the original catalytic solution introduced. The catalyst is then destroyed by any usual means known to the skilled person, and the reaction products and solvent are extracted and separated out.

For a continuous operation, the following is preferably carried out: the catalytic solution is injected at the same time as the ethylene, into a reactor stirred by conventional mechanical means or by external re-circulation, and kept at the desired temperature. The catalyst components can also be separately injected into the reaction medium, for example the product of the interaction of the chromium compound with the aryloxy compound of element M and the hydrocarbylaluminum compound. Ethylene is introduced via a pressure controlled inlet valve, which keeps the pressure constant. The reaction mixture is withdrawn using a liquid level controlled valve to maintain the liquid level constant. The catalyst is continuously destroyed using any means known to the skilled person, then the reaction products and the solvent are separated, for example by distillation. The non-transformed ethylene can be recycled to the reactor The entire disclosure of all applications, patents and publications, cited above and below, and of corresponding French application 99/16509, filed Dec. 24, 1999, are hereby incorporated by reference.

The following examples illustrate the invention without limiting its scope.

EXAMPLE 1

$0.5 \times 10^{-3}$ moles of chromium (III) 2-ethylhexanoate diluted with 25 ml of ortho-xylene that had been distilled and stored under an inert atmosphere was introduced without the ingress of moisture into a 100 ml glass flask placed under an inert atmosphere.

The following were introduced, in order, under an ethylene atmosphere and at room temperature, into a stainless steel autoclave with a working volume of 100 ml provided with a double envelope for regulating the temperature by oil circulation: 5 ml of the chromium (III) 2-ethylhexanoate as prepared above, i.e., $0.1 \times 10^{-3}$ moles of chromium, $0.1 \times 10^{-3}$ moles of bis(2,6-diphenylphenoxy) magnesium in solution in ortho-xylene and $0.3 \times 10^{-3}$ moles of triethylaluminum in solution in ortho-xylene. The temperature was raised to 140° C. and the ethylene pressure was kept at 3 MPa.

After reacting for 30 minutes, ethylene introduction was stopped and the reactor was cooled and degassed, then the gas and liquid, which had been removed with a syringe, were analysed by gas chromatography. 19 g of ethylene had been consumed over 30 minutes. The composition of the products is shown in Table 1. In addition, 11% by weight of polymer was recovered with respect to the ethylene consumed.

EXAMPLE 2

Using the same apparatus as that described for Example 1 and under the same conditions, with the exception that bis(4-t-butyl-2,6-diphenylphenoxy)magnesium was introduced in place of bis(2,6-diphenylphenoxy)magnesium, 5.8 g of ethylene was consumed over a reaction time of one hour. The product composition is shown in Table 1. 12.8% by weight of polymer with respect to the ethylene consumed was also recovered.

EXAMPLE 3

Using the same apparatus as that described for Example 1 and under the same conditions, with the exception that $0.2 \times 10^{-3}$ moles of bis(2,6-diphenylphenoxy)magnesium in solution in ortho-xylene was introduced, along with $0.3 \times 10^{-3}$ moles of triethylaluminum in solution in ortho-xylene, 18.1 g of ethylene was consumed over a reaction time of 30 minutes. The product composition is shown in Table 1. 22.1% by weight of polymer with respect to the ethylene consumed was also recovered.

EXAMPLE 4 (COMPARATIVE)

Using the same apparatus as that described for Example 1 and under the same conditions, with the exception that the magnesium compound was omitted, 1 g of ethylene was consumed over a reaction time of one hour. The product composition is shown in Table 1. 72.5% by weight of polymer with respect to the ethylene consumed was also recovered.

EXAMPLE 5

Using the same apparatus as that described for Example 1 and under the same conditions, with the exception that bis(2-t-butyl-6-phenylphenoxy)magnesium was introduced in place of the bis(2,6-diphenylphenoxy)magnesium, 13.9 g of ethylene was consumed over a reaction time of one hour, The product composition is shown in Table 1. 10.9% by weight of polymer with respect to the ethylene consumed was also recovered.

EXAMPLE 6

Using the same apparatus as that described for Example 1 and under the same conditions, with the exception that bis(2,6-di-t-butylphenoxy)magnesium was introduced in place of the bis(2,6-diphenylphenoxy)magnesium, 5.4 g of ethylene was consumed over a reaction time of one hour. The product composition is shown in Table 1. 20.6% by weight of polymer with respect to the ethylene consumed was also recovered.

EXAMPLE 7

Using the same apparatus as that described for Example 1 and under the same conditions, with the exception that $0.2 \times 10^{-3}$ moles of bis(2,4-di-t-butyl-6-phenylphenoxy) magnesium in solution ortho-xylene was introduced, along with $0.5 \times 10^{-3}$ moles of triethylaluminum in solution in ortho-xylene, 19.5 g of ethylene was consumed over a reaction time of 30 minutes. The product composition is shown in Table 1. 22.7% by weight of polymer with respect to the ethylene consumed was also recovered.

EXAMPLE 8 (COMPARATIVE)

Using the same apparatus as that described for Example 1 and under the conditions given for Example 7, with the exception that $0.2 \times 10^{-3}$ moles of bis(2,4-di-t-butyl-6-phenylphenoxy)isobutyl aluminum in solution in ortho-xylene was introduced in place of the bis(2,4-di-t-butyl-6-phenylphenoxy)magnesium, 13.7 g of ethylene was consumed over a reaction time of one hour. The product composition is shown in Table 1. 31.1% by weight of polymer with respect to the ethylene consumed was also recovered.

TABLE 1

| Example | Oligomer distribution (weight %) | | | | 1-hexene in |
| --- | --- | --- | --- | --- | --- |
| | C4 | C6 | C8 | C10+ | C6 (weight %) |
| 1 | 1.3 | 84.4 | 1 | 2.3 | 98.9 |
| 2 | 1.1 | 82.7 | 1.1 | 2.4 | 99.7 |
| 3 | 1.7 | 70.2 | 2 | 3.9 | 98.4 |
| 4 | 20 | 5 | 0.5 | 2 | 55.0 |
| 5 | 0.6 | 85.4 | 0.7 | 2.4 | 99.4 |
| 6 | 2.3 | 74.2 | 0.6 | 2.4 | 95.2 |
| 7 | 1.7 | 70.5 | 1.6 | 3.5 | 98.0 |
| 8 | 2.6 | 61.1 | 1.1 | 4.1 | 97.3 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A catalytic composition, obtained by mixing:
    at least one catalyst-forming chromium compound;
    with at least one aryloxy compound of an element M selected from the group consisting of magnesium, calcium, strontium and barium, with general formula $M(RO)_{2-n}X_n$, where RO is an aryloxy radical containing 6 to 80 carbon atoms, X is a halogen or a hydrocarbyl radical containing 1 to 30 carbon atoms and n is a whole number that is 0 or 1; and
    with at least one aluminum compound selected from the group consisting of ethylaluminum sesquichloride, tris (hydrocarbyl)aluminum compounds, chlorinated and brominated hydrocarbylaluminum compounds, with general formula $AlR'_m Y_{3-m}$, where R' is a hydrocarbyl radical containing 1 to 6 carbon atoms, Y is a chlorine or bromine atom and m is a number from 1 to 3, and aluminoxanes.

2. A composition according to claim 1 wherein the aryloxy radical RO in the aryloxy compound of element M with general formula $M(RO)_{2-n}X_n$ has general formula:

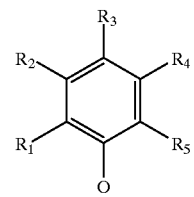

where $R_1$, $R_2$, $R_3$, $R_4$ and $R_5$, which may be identical or different, represent a hydrogen atom, a halogen atom or a hydrocarbyl radical containing 1 to 16 carbon atoms.

3. A composition according to claim 1, wherein the aryloxy compound of element M is bis(2,6-diphenylphenoxy)magnesium, bis(2-tert-butyl-6-phenylphenoxy)magnesium or bis(2,4-di-tert-butyl-6-phenylphenoxy)magnesium.

4. A composition according to claim 3, wherein the hydrocarbylaluminum compound is triethylaluminum.

5. A composition according to claim 1, wherein the hydrocarbylaluminum compound is dichloroethylaluminum, ethylaluminum sesquichloride, chlorodiethylaluminum, chlorodiisobutylaluminum, triethylaluminum, tripropylaluminum, triisobutylaluminum or methylaluminoxane.

6. A composition according to claim 1, wherein the hydrocarbylaluminum compound is triethylaluminum.

7. A composition according to claim 1, wherein the components of the catalyst are brought into contact in a solvent comprising at least one saturated hydrocarbon, at least one unsaturated olefinic or diolefinic hydrocarbon and/or at least one aromatic hydrocarbon.

8. A composition according to claim 7, wherein the chromium concentration in the catalytic solution is in the range $1 \times 10^{-5}$ to 0.1 mole/l.

9. A composition according to claim 1, wherein the mole ratio between the aryloxy compound of element M and the chromium compound is 1:1 to 30:1, and the mole ratio between the hydrocarbylaluminum compound and the chromium compound is 1:1 to 35:1.

10. A composition according to claim 1, wherein the chromium compound comprises one or more identical or different anions selected from the group consisting of halides, carboxylates, acetylacetonates, alkoxy and aryloxy anions.

11. A composition according to claim 10, wherein the aryloxy radical RO in the aryloxy compound of element M with general formula $M(RO)_{2-n}X_n$ has general formula:

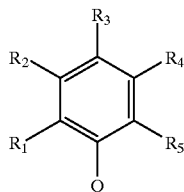

where $R_1$, $R_2$, $R_3$, $R_4$ and $R_5$, which maybe identical or different, represent a hydrogen atom, a halogen atom or a hydrocarbyl radical containing 1 to 16 carbon atoms.

12. A composition according to claim 11, wherein the hydrocarbylaluminum compound is dichloroethylaluminum, ethylaluminum sesquichloride, chlorodiethylaluminum, chlorodiisobutylaluminum, triethylaluminum, tripropylaluminum, triisobutylaluminum or methylaluminoxane.

13. A composition according to claim 10, wherein the aryloxy compound of element M is bis(2,6-diphenylphenoxy)magnesium, bis(2-tert-butyl-6-phenylphenoxy)magnesium or bis(2,4-di-tert-butyl-6-phenylphenoxy)magnesium.

14. A composition according to claim 13, wherein the hydrocarbylaluminum compound is triethylaluminum.

15. A composition according to claim 14, wherein the components of the catalyst are brought into contact in a solvent comprising at least one saturated hydrocarbon, at least one unsaturated olefinic or diolefinic hydrocarbon and/or at least one aromatic hydrocarbon.

16. A composition according to claim 15, wherein the chromium concentration in the catalytic solution is in the range $1 \times 10^{-5}$ to 0.1 mole/l.

17. A composition according to claim 15, wherein the mole ratio between the aryloxy compound of element M and the chromium compound is 1:1 to 30:1, and the mole ratio between the hydrocarbylaluminum compound and the chromium compound is 1:1 to 35:1.

18. A composition according to claim 10, wherein the hydrocarbylaluminum compound is dichloroethylaluminum, ethylaluminum sesquichloride, chlorodiethylaluminum, chlorodiisobutylaluminum, triethylaluminum, tripropylaluminum, triisobutylaluminum or methylaluminoxane.

19. A composition according to claim 18, wherein the hydrocarbylaluminum compound is dichloroethylaluminum, ethylaluminum sesquichloride, chlorodiethylaluminum, chlorodiisobutylaluminum, triethylaluminum, tripropylaluminum, triisobutylaluminum or methylaluminoxane.

20. A composition according to claim 10, wherein the components of the catalyst are brought into contact in a solvent comprising at least one saturated hydrocarbon, at least one unsaturated olefinic or diolefinic hydrocarbon and/or at least one aromatic hydrocarbon.

21. A composition according to claim 20, wherein the chromium concentration in the catalytic solution is in the range $1 \times 10^{-5}$ to 0.1 mole/l.

22. A composition according to claim 20, wherein the mole ratio between the aryloxy compound of element M and the chromium compound is 1:1 to 30:1, and the mole ratio between the hydrocarbylaluminum compound and the chromium compound is 1:1 to 35:1.

23. In a process comprising oligomerization ethylene in contact with a catalytic under oligomerization conditions, the improvement wherein the catalyst is a catalytic composition according to claims 1.

24. A process according to claim 23, wherein the ethylene oligomerization reaction is carried out at a pressure of 0.5 to 15 MPa and at a temperature of 20° C. to 180° C.

25. A process according to claim 23, wherein the chromium compound comprises one or more identical or different anions selected from the group consisting of halides, carboxylates, acetylacetonates, alkoxy and aryloxy anions.

26. A process according to claim 23, wherein the aryloxy radical RO in the aryloxy compound of element M with general formula $M(RO)_{2-n}X_n$ has general formula:

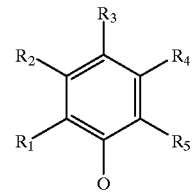

where $R_1$, $R_2$, $R_3$, $R_4$ and $R_5$, which may be identical or different, represent a hydrogen atom, a halogen atom or a hydrocarbyl radical containing 1 to 16 carbon atoms.

27. A process according to claim 23, wherein the aryloxy compound of element M is bis(2,6-diphenylphenoxy)magnesium, bis(2-tert-butyl-6-phenylphenoxy)magnesium or bis(2,4-di-tert-butyl-6-phenylphenoxy)magnesium.

28. A process according to claim 23, wherein the hydrocarbylaluminum compound is dichloroethylaluminum, ethylaluminum sesquichloride, chlorodiethylaluminum, chlorodiisobutylaluminum, triethylaluminum, tripropylaluminum, triisobutylaluminum or methylaluminoxane.

29. A process according to claim 23, wherein the hydrocarbylaluminum compound is triethylaluminum.

30. A process according to claim 23, wherein the chromium concentration in the catalytic solution is in the range $1 \times 10^{-5}$ to 0.1 mole/l.

31. A process according to claim 23, wherein the mole ratio between the aryloxy compound of element M and the chromium compound is 1:1 to 30:1, and the mole ratio between the hydrocarbylaluminum compound and the chromium compound is 1:1 to 35:1.

32. A process according to claim 23, wherein the aryloxy compound of element M is bis(2,6-diphenylphenoxy)magnesium, bis(2-tert-butyl-6-phenylphenoxy)magnesium or bis(2,4-di-tert-butyl-6-phenylphenoxy)magnesium and wherein the hydrocarbylaluminum compound is triethylaluminum.

33. A process of making the composition of claim 1, comprising first mixing the chromium compound with the aryloxy compound of element M and thereafter adding the hydrocarbylaluminum compound.

* * * * *